United States Patent [19]
Ichien

[11] Patent Number: 5,444,248
[45] Date of Patent: Aug. 22, 1995

[54] METHOD AND APPARATUS FOR CHECKING THE CONDITION OF ADHESIVE APPLICATION IN PACKAGES

[75] Inventor: Kenji Ichien, Shiga, Japan
[73] Assignee: Optex Co., Ltd., Shiga, Japan
[21] Appl. No.: 205,970
[22] Filed: Mar. 3, 1994
[30] Foreign Application Priority Data
   Mar. 4, 1993 [JP] Japan ................. 5-043431
[51] Int. Cl.6 .................. G01J 5/10; G01N 25/72
[52] U.S. Cl. .................. 250/342; 250/338.1; 250/358.1; 250/359.1
[58] Field of Search .............. 250/342, 338.1, 358.1, 250/359.1

[56] References Cited
U.S. PATENT DOCUMENTS
4,831,258 5/1989 Paulk et al. .............. 250/349
5,026,989 6/1991 Merkel .............. 250/338.1
5,323,005 6/1994 Merkel .............. 250/342

Primary Examiner—Carolyn E. Fields
Attorney, Agent, or Firm—Panitch, Schwarze Jacobs & Nadel

[57] ABSTRACT

Method and apparatus for checking the condition of adhesive application in the form of beads on packages, characterized by the steps of causing each package to pass through a light reception area of an infrared sensor so as to receive infrared energy radiating from the beads on the package, detecting a signal output by the sensor in response to the received energy so as to measure at least one of a peak value corresponding to the rise of the received energy, a peak value corresponding to the fall thereof, and a period of time from the rise to the fall; and comparing an obtained value with a reference value so as to determine the condition of the beads.

6 Claims, 6 Drawing Sheets

Fig. 3

METHOD AND APPARATUS FOR CHECKING THE CONDITION OF ADHESIVE APPLICATION IN PACKAGES

BACKGROUND OF THE INVENTION

The present invention relates generally to a system for checking the condition or quality of adhesive application on an automatic merchandize packaging line.

On the automatic merchandize packaging line thermal adhesive is applied to the flaps of the packages, mainly made of cardboard, spot by spot by means of a gun or the like. The deposit of adhesive in each spot form a bead so that as a whole a plurality of beads are aligned along the edges of tile flaps of packages. In this way the flaps of the packages are heat sealed. However, a problem arises in automatically applying adhesive on the flaps spot by spot in that the amount of applied adhesive tends to be irregular from bead to bead, in some beads short and others excessive. When the amount is short, it results in poor bond between the flaps. When it is excessive, it causes smearing and stains the packages. What is worse, smeared adhesive causes the packages to stick to other objects. Therefore, constant care must be taken to check the condition or quality of beads on the flaps of packages.

In order to monitor, a photoelectric switch is proposed for being placed along the operation line to find any poor or improper beads. However, the monitoring results are subject to photoelectricity whose intensity depends upon the nature and quality of the cardboard of which the packages are made, thereby failing to obtain precise data. As an alternative, a monitor camera is proposed whereby the condition of beads is visually inspected through a picture. However, the picture is not always clear, and in order to effect precise inspection, an expensive detector must be additionally equipped. Thus the cost is increased.

Another monitoring method is disclosed in the Japanese Publication (allowed) No. 4-51415, which is designed to find a defective bead by reference to temperatures of the beads. More specifically, it is ascertained whether or not each bead has adhesive and how many beads are formed, by counting signals from an infrared sensor for sensing the temperatures of the beads. However, this method is only to check the presence of adhesive in each spot but cannot inspect the condition or quality of adhesive application in each spot.

SUMMARY OF THE INVENTION

According to the present invention, there is provided a method which includes the steps of causing each package to pass through a light reception area of an infrared sensor so as to receive infrared energy radiating from the beads on the package, detecting a signal output by the sensor in response to the received energy so as to measure at least one of a peak value corresponding to the rise of the received energy, a peak value corresponding to the fall thereof, and a period of time from the rise to the fall; and comparing an obtained value with a reference value so as to determine the condition of the beads.

The signal responsive to the received energy may be amplified at a given ratio, or additionally, be differentiated into a differential waveform signal indicating time-varying rate of each signal.

According to another aspect of the present invention, there is provided an apparatus which includes an infrared sensor having a light reception area for sensing infrared energy radiating from the beads on the packages passing through the light reception area and at the same time, outputting a signal in response to the received energy, a comparator for comparing the signal with a predetermined reference value so as to evaluate the condition of the beads.

Preferably, the apparatus includes an amplifier for amplifying the signal or additionally a differentiating circuit so as to obtain a differential waveform signal.

BRIEF DESCRIPTION OF THE DRAWINGS

FIG. 3 is a view exemplifying the manner to evaluate the condition of beads according to the present invention;

DESCRIPTION OF THE PREFERRED EMBODIMENT

Figure 1:
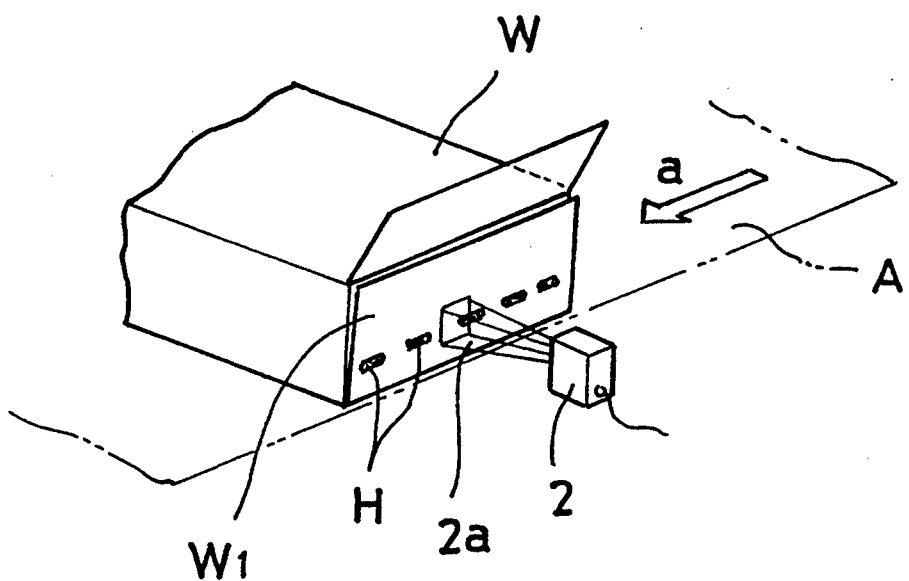
FIG. 1 is a perspective view showing a state in which beads on the package flap are inspected by an infrared sensor (acceptor)
Figure 2:
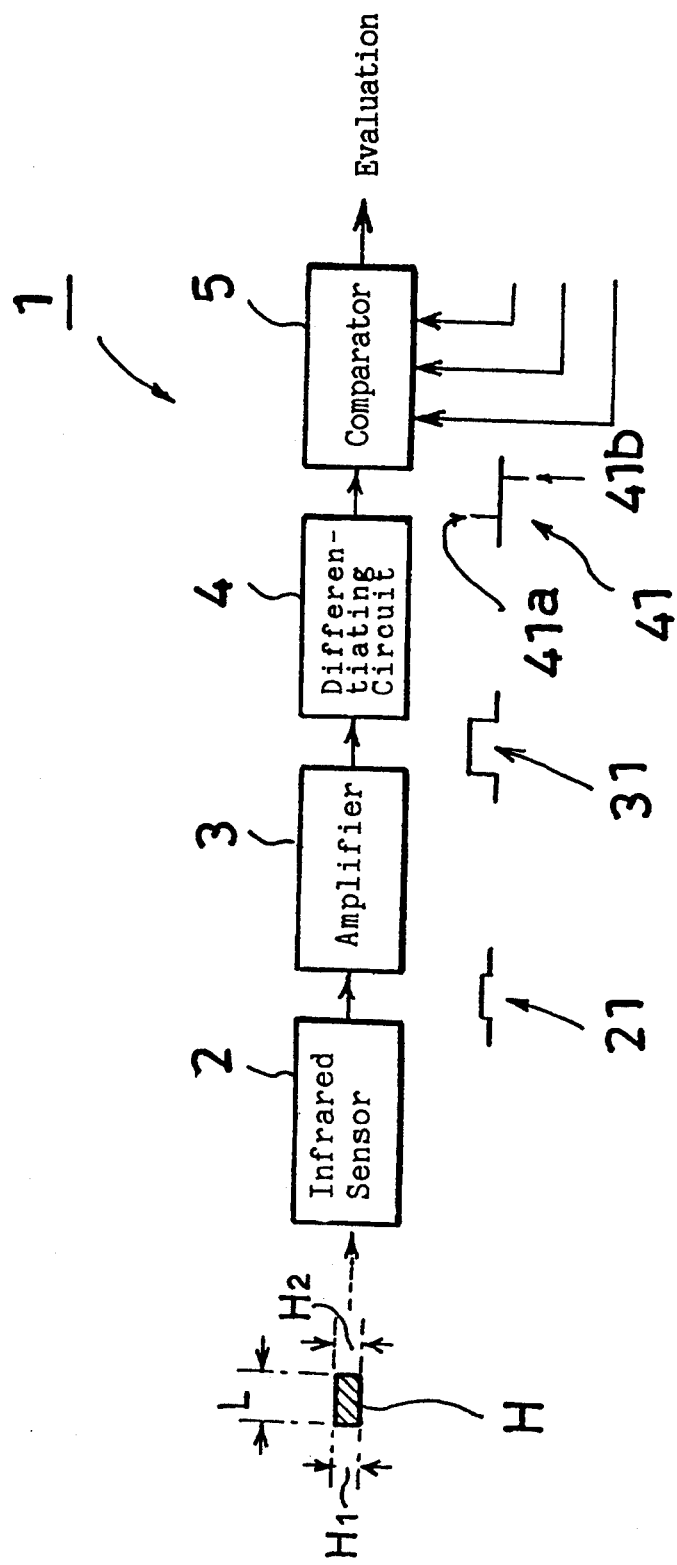
FIG. 2 is a block diagram showing a process of evaluating the condition of beads.

Referring to FIGS 1 and 2, the exemplary apparatus 1 includes an infrared sensor (acceptor) 2, an amplifier 3, a differentiating circuit a and a comparator 5. Each of these components will be described in detail:

The infrared sensor 2 is connected to the amplifier 3 which amplifies an output from the sensor 2 at a given rate. The amplifier 3 is connected to the differentiating circuit a which is connected to the comparator 5 which compares a peak value of the signal from the differentiating circuit 4. A package (W) is transferred by a conveyor (A) in a direction indicatect by the arrow (a). The package (W) has two foldable flaps of which the inner flap (W1) has beads (H) having the deposit of adhesive. The adequacy of beads (H) is inspected by the sensor 2 by receiving infrared radiating from each bead (H), and generates signals 21 whose magnitudes depend on the sensing energy. The amplifier 3 amplifies the signals 21 at a given rate ratio to obtain an amplified signal 31 which is then differentiated by the differentiating circuit 4 so as to generate a differentiating waveform signal 41 indicating a time variation of the signal 31. Since the signal 41 indicates a time variation of the amplified signal 31, it depends upon the condition of the beads (H); generally, the signal 41 has an initial peak 41a and a final peak 41b corresponding to the rise and fall of the signal 31, respectively.

The comparator 5 is constructed so as to receive an upper limit and a lower limit (reference values) of each of a first, second and third predetermined range which may be evaluated as being "normal" with respect to the height ($H_1$) of the starting end and the height ($H_2$) of the terminating end of each bead (H), and the length (L) of each bead, as shown in FIG. 2.

The comparator 5 compares the initial peak value 41a of the differentiated waveform signal 41 with the upper limit and lower limit of the first reference range, and at the same time compares the final peak value 41b with the upper limit and lower limit of the second reference range.

An example of performing the method of the present invention will be described, wherein a temperature drop of each bead (H) occurring during the passage of it through a light reception area 2a will be ignored:

Merchandise such as electronic components, food, canned liquid, is packed in a package (W) and an adhesive is applied to a dust flap or merely flap ($W_1$) of the package (W) spot by spot by means of a gun. Then, as shown in FIG. 1, the package (W) is transported by the conveyor (A) in the direction of arrow (a) and passes through the light reception area 2a of the infrared sensor 2. At this stage, the bead (H) has a temperature higher than the ambience, and radiates infrared ray corresponding to its temperature. The sensor 2 senses the infrared ray, and outputs a signal 21 whose magnitude depends upon the energy of the received ray. The energy varies in accordance with the temperatures, sizes and shapes of the beads. Thus the signal 21 forms a waveform representing the condition of the beads on the flaps of packages. More specifically, as shown in FIG. 2, the low height ($H_1$) of the bead (W) indicates that the waveform is small, and the large height ($H_1$) indicates that the waveform is large. The long length (L) indicates that the waveform extends lengthwise.

Preferably, the signal 21 (hereinafter referred to as "pre-amplified signal") can be amplified by the amplifier 3 at a predetermined ratio to make a signal 31 (hereinafter referred to as "amplified signal"), and then be input to the differentiating circuit 4 hereby the amplified signal 31 is converted into a differential waveform signal 41 representing the time variation of the amplified signal 31. The differential waveform signal is input to the comparator 5.

The differential waveform 41 has two peaks 41a, 41b at its starting end which correspond to the rise and fall of the amplified signal 31. For explanation sake, suppose that the heights of the peaks 41a and 41b, that is, peak values, be a first value and a second value, respectively, and that the period of time from the peak 41a to the peak 41b be a third value. The first and second values correspond to the amount of the received energy and the third value corresponds to the length (L) detected in the direction of arrow (a) in which the package (W) is advanced. Any difference between the first and second values indicates that the bead heights (H) are not uniform. Non-difference indicates that the heights (H) are the same.

After receiving data about the condition of beads in the form of differential waveform signals, the comparator 5 compares each of the first, second and third values with the upper limit and the lower limit to see whether or not they fall within each reference range. Each of the first, second and third reference ranges represents a "normal" zone in which the beads may be considered to be in normal condition. In this way, when the first value falls within the first reference range, the height ($H_1$) may be evaluated as "normal". Likewise, when the second value falls within the second reference range, the height ($H_2$) may be evaluated as "normal". When the third value falls within the third reference range, the length (L) of the bead (W) in the advancing direction thereof may be evaluated as "normal". Depending upon the packages, all of the results can be adopted or else one or two of the results can be adopted so as to see whether the beads is in normal condition or not.

The amplified signals 31 are transformed into differential waveform signals 41, thereby eliminating the necessity of using a chopper which otherwise would be used to chop inputs in synchronism with passage through the light reception area and remove impure components such as influences of the ambient temperature. As a result, the production cost is saved, and the long-term reliability is guaranteed.

Figure 3:
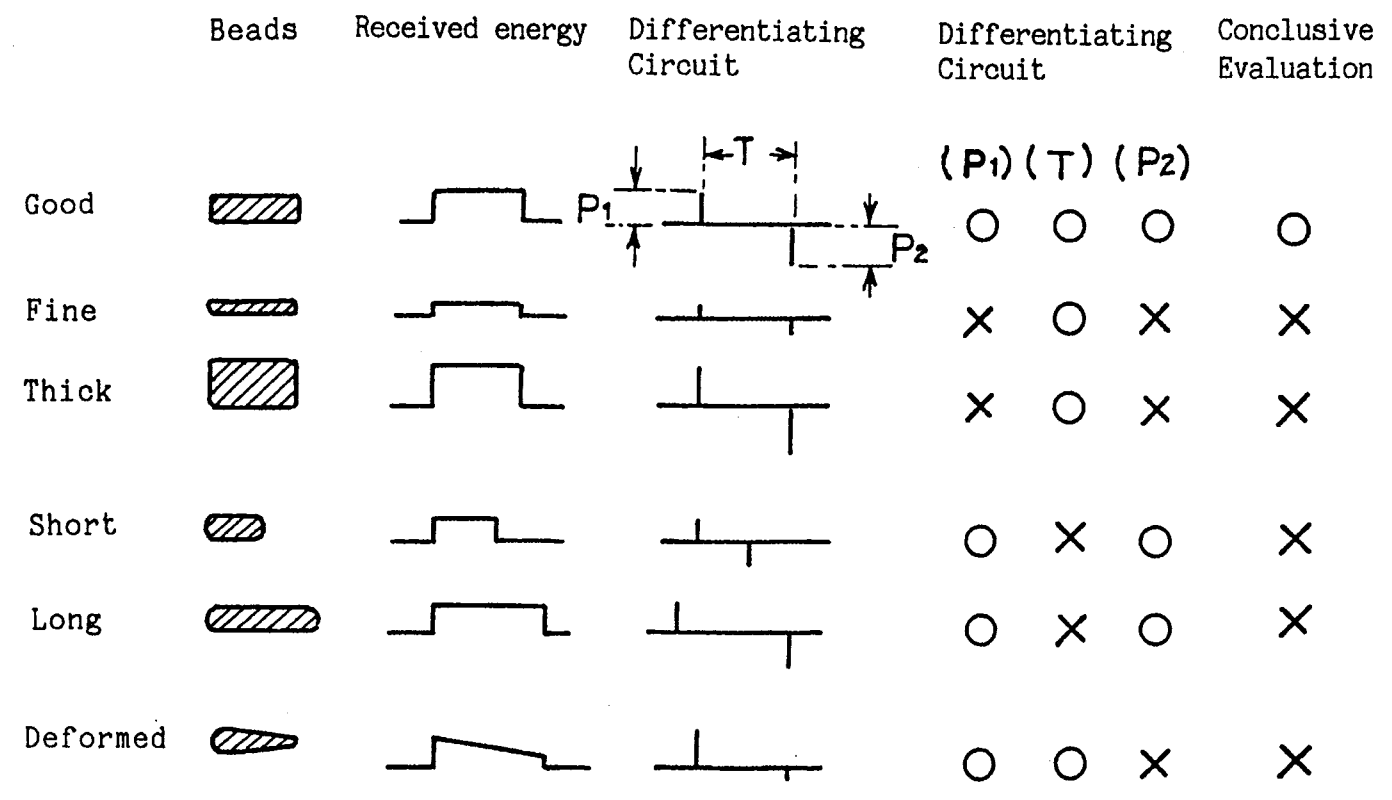

Referring to FIG. 3, a typical example of evaluating the condition of beads will be described:

Six kinds of beads are illustrated together with the corresponding waveform signals, wherein the symbol ◯ means "normal", and the symbol (X) means "poor". The conclusive evaluation is based on the evaluating symbols considered together for $P_1$, $P_2$ and L. Even if one or two of $P_1$, $P_2$ and L are found to be "normal (◯)", the conclusive evaluation amounts to "poor(X)". Under the known practice of evaluation at least one normal would mean that the bead is in normal condition. The present invention can provide a more strict standard for testing the quality of beads; that is, it is possible to evaluate the bead as normal only when $P_1$, $P_2$, and H are all found "normal". The following standards are possible and can be selected as the case may be:

(1) When the first value ($P_1$) falls within the first reference range, the bead is wholly evaluated as normal, wherein the bead has a starting height falling within the normal range;

(2) When the second value ($P_2$) falls within the second reference range, the bead is wholly evaluated as normal, wherein the bead has a terminating height falling with the "normal" range;

(3) When the third value (L) falls within the third reference range, the bead is wholly evaluated as normal, wherein the bead has a length in the advancing direction.

Alternatively, two of the standards (1) to (3) can be alternatively combined as follows:

(4) When the first value ($P_1$) falls within the first reference range, and when the second value ($P_2$) falls within the second reference range, the bead is wholly evaluated as normal;

(5) When the second value ($P_2$) falls within the second reference range, and when the third value (L) fails within the third reference range, the bead is wholly evaluated as normal.

(6) When the first value ($P_1$) falls within the first reference range, and when the third value (L) falls within the third reference range, the bead is wholly evaluated as normal.

It is possible to evaluate a bead on the basis of the comparison of any of the peak values ($P_1$), ($P_2$) and the length (L) with the respective reference range.

In the illustrated embodiment it is presumed that a temperature drop in the bead is negligible but if temperature drop is so large from the rise to the fall of the received energy that a peak value at the fall becomes too small, the peak values and reference range can be compensated by a value corresponding to the temperature drop.

Figures 4A, 4B:
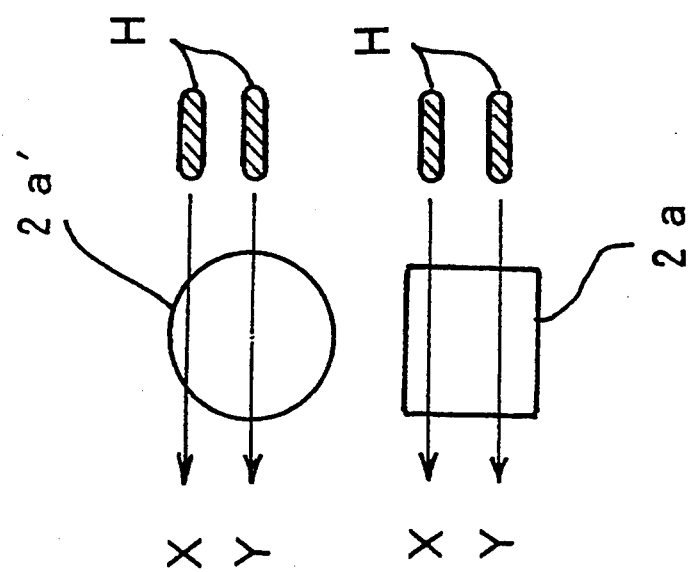
FIG. 4A is a view exemplifying a light reception area of the sensor.
FIG. 4B is a view exemplifying another type of light reception area of the sensor.
Figure 5:
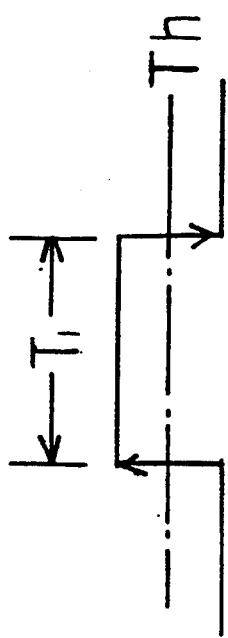
FIG. 5 is a waveform of an output from a sensor under a second example of the embodiment.

The light reception area 2a is preferably rectangular as shown in FIG. 4(B) instead of being circular shown in FIG. 4(A). In the circular shape light rays x and y pass through the peripheral portion and the central portion of the area for different periods of time. In contrast, the rectangular area 2a permits the light rays x and y to pass for the same period of time, thereby maintaining stabilized detection even if the beads are not in perfect alignment with the light reception area 2a.

Figure 6:
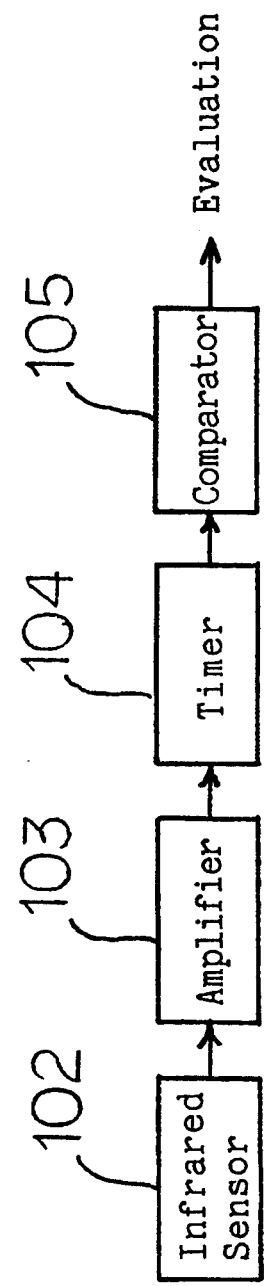
FIG. 6 is a block diagram showing a process of evaluating the condition of beads under the second example.

Referring to FIG. 6, a second example will be described:

The system of this example includes an infrared sensor 102, an amplifier 103, a timer 104 and a comparator 105. This system enables the evaluation of beads without the use of the differential waveform signals. More specifically, the sensor 102 outputs a signal in response to the reception of infrared energy from the bead. The timer 104 starts when the signal rises above a predetermined threshold Th, and stops when it falls below it. In this way a time T1 from the rise to the fall of the signal is measured from which the length of the bead is measured.

Figure 7:
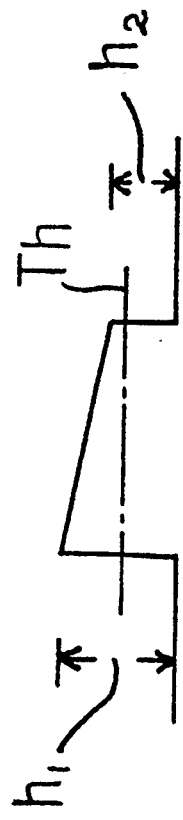
FIG. 7 is a waveform of an output from a sensor under a third example of the embodiment.
Figure 8:
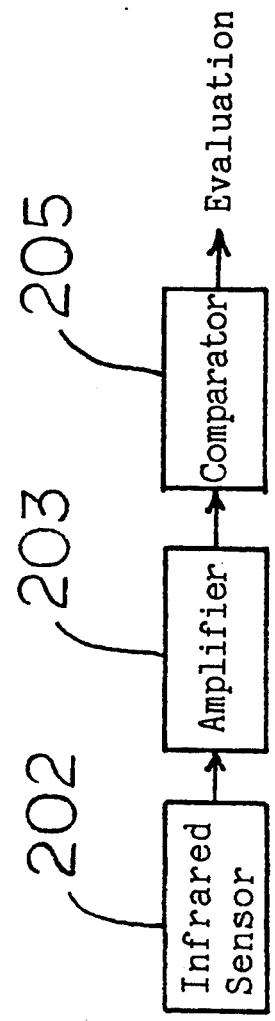
FIG. 8 is a block diagram showing a process of evaluating the condition of beads under the third example.

Referring to FIGS. 7 and 8, a third example will be described:

This system includes an infrared sensor 202, an amplifier 203, and a comparator 205. A peak value h, resulting when the signal rises above a predetermined threshold Th, and a peak value $h_2$ immediately before the signal falls below it are compared by the comparator 205.

The comparators 105 and 205 are constructed to allow predetermined reference values to be input although the details are not shown.

What is claimed is:

1. A method for checking the condition of beads on packages, the method comprising the steps of:

causing each package to pass through a light reception area of an infrared sensor so as to receive infrared energy radiating from the beads on the package;

detecting a signal output by the sensor in response to the received energy so as to measure at least one of a peak value corresponding to the rise of the received energy, a peak value corresponding to the fall thereof, and a period of time from the rise to the fall;

differentiating the signal into a differential waveform signal; and comparing at least one value obtained from the differential waveform signal with a corresponding reference value so as to determine the condition of the beads.

2. The method according to claim 1, further comprising the step of amplifying the signal at a predetermined ratio prior to comparing the obtained value with a reference value.

3. The method according to claim 1, wherein the light reception area is rectangular.

4. An apparatus for checking the condition of beads on packages, the apparatus comprising:

an infrared sensor having a light reception area for sensing infrared energy radiating from the beads on the packages passing through the light reception area and at the same time, outputting a signal in response to the received energy;

a differentiating circuit for differentiating the signal into a differential waveform signal; and a comparator for comparing at least one value obtained from the differential waveform signal with a predetermined reference value so as to evaluate the condition of the beads.

5. The apparatus according to claim 4, further comprising an amplifier for amplifying the signal at a predetermined ratio prior to comparing the signal with a reference value so as to evaluate the condition of the beads.

6. The apparatus according to claim 4, wherein the light reception area is rectangular.

* * * * *